United States Patent [19]
Aldrich et al.

[11] Patent Number: 5,049,489
[45] Date of Patent: Sep. 17, 1991

[54] 16S RRNA OLIGONUCLEOTIDE PROBES FOR THE IDENTIFICATION OF SULFATE-REDUCING BACTERIA

[75] Inventors: Kathryn J. Aldrich, Cleveland Heights; Donald E. Brink, Valley View, both of Ohio

[73] Assignee: The Standard Oil Company, Cleveland, Ohio

[21] Appl. No.: 339,277

[22] Filed: Apr. 17, 1989

[51] Int. Cl.$^5$ ...................... C12Q 1/68; C07H 15/12; C12N 15/00
[52] U.S. Cl. .......................................... 435/6; 536/27; 935/77; 935/78
[58] Field of Search ..................... 435/6, 253; 436/501; 536/27; 935/77, 78

[56] References Cited

U.S. PATENT DOCUMENTS

| | | | |
|---|---|---|---|
| 4,358,535 | 9/1982 | Falkow et al. | 435/5 |
| 4,556,643 | 12/1985 | Paau et al. | 436/501 |
| 4,562,156 | 4/1985 | Isbister et al. | 435/253 |
| 4,563,419 | 1/1986 | Ranki et al. | 435/6 |
| 4,582,789 | 9/1986 | Sheldon, III et al. | 436/501 |
| 4,599,303 | 11/1986 | Yabusaki et al. | 435/6 |
| 4,626,501 | 8/1986 | Landes | 435/6 |
| 4,677,054 | 6/1987 | White et al. | 435/6 |
| 4,717,653 | 10/1988 | Webster, Jr. | 435/5 |

FOREIGN PATENT DOCUMENTS 0167366 7/1986 European Pat. Off. .
0229442 10/1987 European Pat. Off. .

OTHER PUBLICATIONS

Oyaizu et al., System. Appl. Microbiol., 6:257–263, (1985).
Ivanov et al., Gene, 46:287–290 (1986).
International Journal of Systematic Bacteriology, Apr. 1987, pp. 116–122, Stahl et al., "Phylogenetic Analysis of Certain Sulfide-Oxidizing . . .".

Primary Examiner—Robert A. Wax
Assistant Examiner—Mindy B. Fleisher
Attorney, Agent, or Firm—Nixon & Vanderhye

[57] ABSTRACT

Oligonucleotide probes complementary to the 16S rRNA molecule, suitably labelled, that bind to a characteristic portion of the 16S rRNA molecule of spore-forming sulfate reducing bacterial (SRB) and/or the non-spore forming SRB, Desulfovibrio desulfuricans, are described. The use of these probes in conjunction with "negative control probes" to detect these bacteria in the oilfield as well as any other environment in qualitative and quantitative assays is described. Use of "Universal C" primer as a probe to detect all bacteria for total bacterial assays in environmental samples is described.

8 Claims, 7 Drawing Sheets

16S RRNA OLIGONUCLEOTIDE PROBES FOR THE IDENTIFICATION OF SULFATE-REDUCING BACTERIA

BACKGROUND OF THE INVENTION

This invention relates to procedures for detecting and identifying sulfate-reducing bacteria, or SRBs, and more particularly, to the use of oligonucleotide probes complementary to portions of the 16S rRNA molecule of these bacteria to detect and identify sporing and non-sporing sulfate-reducing bacteria.

Sulfate-reducing bacteria, such as members of the genera Desulfovibrio and Desulfotomaculum, reduce sulfate and/or sulfite under suitable anaerobic conditions, which leads to corrosion of iron-containing materials with which the bacteria are in contact, for example metal structures and conduits, and generate hydrogen sulfide, an odiferous, poisonous gas. Sulfate- reducing bacteria are also present in other systems, for example *Desulfotomaculum ruminis* is present in the rumen of ruminant animals, particularly cattle.

The presence of sulfate-reducing bacteria in many environments is undesirable, particularly in concentrations sufficient to cause significant corrosion of iron-containing metals in contact with SRB-containing aqueous solutions including fresh and sea waters. It is common practice to control SRB growth by adding an antimicrobial composition to the aqueous solutions containing them. However, antimicrobials are costly and therefore must be applied judiciously. Monitoring of the system to detect population density changes is a common practice, and antimicrobials are added either continuously or after the population density reaches certain levels.

In addition to causing corrosion of iron-containing metals, sulfate-reducing bacteria are largely responsible for generating hydrogen sulfide gas, a foul-smelling gas which is toxic at very low concentrations. SRBs are often present in a producing oil well which over a period of time "sours" and produces hydrogen sulfide gas which lowers the value of the oil. The presence of hydrogen sulfide in crude oil requires the use of precautions and protective measures for possible worker exposure to hydrogen sulfide gas thus the rapid identification and quantitation of SRBs is important to occupational safety.

In contrast to their undesired presence, SRBs are also present in the gut of ruminant animals, particularly domestic animals (cattle) used as protein sources for human consumption. Prepared animal feeds customarily contain antibiotics added as a prophylactic to prevent animal infections especially when the animal is moved from one feeding location to another. These feed additive antibiotics, sometimes called pro-biotics, may upset the animal's natural intestinal flora, which includes sulfate-reducing bacteria. A means to assess and monitor these bacteria and compare them to the pro-biotic selection and ingestion is also desirable. The above are but two illustrations of the applicability of the procedures of this invention and are not intended to be limiting.

By "sulfate-reducing bacteria" we mean bacteria capable of reducing sulfate to sulfite and/or sulfite to sulfide regardless of the taxonomic group of the bacteria.

Sulfate-reducing bacteria are a major source of corrosion in oilfield production waters, thus it is necessary to reduce their presence. A biocide may be used to control the growth of sulfate-reducing bacteria. Commonly, biocide is added to the water when the bacterial cell density exceeds a predetermined level, or biocide may be injected continuously. The current method of detecting the SRB cell level is by serial dilution in culture medium to detect cell growth, in which water samples are serially diluted into nutrient SRB medium and FeS production is observed by the formation of black precipitate. Commonly known as the American Petroleum Institute (API) method, obtaining results from this serial dilution assay may take as long as three to four weeks.

BRIEF DESCRIPTION OF THE DRAWINGS

FIG. 1 shows the nucleotide sequences of the 16S rRNA molecule from ATCC deposit 19858, a spore-forming sulfate-reducing bacterium, shown folded into secondary structure. This structure was compared to other 16S rRNA sequences to locate regions and specific nucleotide sequences that are shared among sporing SRBs yet not found in the 16S rRNA of other bacteria and used as a model from which to construct oligonucleotide probes in accordance with this invention.

DESCRIPTION OF THE INVENTION

We describe oligonucleotide probes specifically tailored to selectively identify two groups of sulfate-reducing bacteria: (a) spore-formers and (b) non-spore-formers that we are treating as *Desulfovibrio desulfuricans*. These probes are designed for minimal reactivity with 16S rRNA of other bacteria that may be present in a test sample, and to rapidly and accurately quantify these two groups of sulfate-reducing bacteria. Described are oligonucleotide probes based on the 16S rRNA molecule and include both novel 16S rRNA oligonucleotide probes designed to detect the above named sulfate-reducing bacteria, and a known 16S rRNA oligonucleotide probe designed to detect all bacteria.

Oligonucleotide probe design is based upon identification of regions of the 16S rRNA molecule that are (a) so variable among bacterial taxa that species or even sub-species may be identified or (b) variable, but conserved among groups of related orgnaisms as described by Woese in *Microbiol. Rev.* 51:221-271 (1987) and Woese et al., in *System. Appl. Microbiol.* 6:143-151 (1985). Application of oligonucleotide probes complementary to regions of the 16S rRNA molecule for the identification of specific organisms or groups of organisms has been described by Gobel et al. in *J. Gen. Microbiol* 133:1969-1974 (1987), Haun and Gobel in *FEMS Microbiol. Letters* 43:187-193 (1987), Giovannoni et al. in *J. Bacteriol.* 170:720-726 (1988) and Stahl et al. in *Appl. and Environ. Microbiol.* 54:1079-1084 (1988). These authors recognized the value in targeting the 6S rRNA molecule because it contains ribonucleotide sequences unique to particular taxa, and because this molecule is present at about 10,000-20,000 copies per cell as described in Stahl, (1986) *Bio/technology* 4:623-628. There are only about 7 copies of the 16S rRNA gene in the genome (Ingraham et al., 1983, Growth of the Bacterial Cell), and thus the rRNA targets are greatly amplified by comparison.

This invention enables a quick means to identify a class of bacteria of specific interest and arises from procedures used to classify organisms taxonomically. Elucidation of phylogenetic relationships among organisms has been greatly aided by analysis of rRNA because the sequences encoding rRNAs change very slowly compared to most proteins (reviewed in Fox et al., *Sci.* 209:459–483 (1980)). In particular, the approximately 1600 nucleotide-long 16S rRNA gene has been used extensively to ascertain bacterial phylogenies in a procedure known as 16S rRNA oligonucleotide catalog analysis. In practice, $^{32}$P-labelled 16S rRNA is digested with ribonuclease T1 (which cleaves the molecule at G residues) and the resulting short fragments of up to 20 nucleotides are separated by two dimensional paper electrophoresis and are subsequently sequenced. A catalog of these sequences unique to the organism is produced. Direct sequencing of the 16S rRNA molecule using methods like those described in Lane et al., *Proc. Natl. Acad. Sci. USA* 82:6955–6959 (1985), has largely replaced oligonucleotide catalog analysis.

Comparison of the 16S rRNA sequences, some of which are highy conserved among all organisms, and some are divergent, can be used to assess the phylogenetic relatedness between the organisms. Using this technique, some 400 bacterial species have been analyzed, including the delta group of the purple bacteria, a newly recognized group composed of the sulfur- and sulfate-reducing bacteria myxobacteria, and bdellovibrios, as described by Oyaizu and Woese, *System. Appl. Microbiol.* 6:257–263 (1985). The sulfate-reducing bacteria in this group of purple bacteria are non-spore forming, gram-negative and grow at mesophilic temperatures. Fowler et al., *System. Appl. Microbiol* 8:32–41 (1986) recognized seven genera that included Desulfovibrio, Desulfococcus, Desulfosarcina, Desulfomonas, Desulfobulbus, Desulfonema and Desulfobacter. Another group of SRBs has been defined as belonging to the genus Desulfotomaculum. This genus is spore-forming, grows at thermophilic temperatures and although it is gram-negative, it is currently classified as one of several major sublines within the Clostridium subdivision of the gram-positive eubacteria as reviewed by Fowler at al (supra). Both the spore-forming and non-spore-forming groups of SRBs have been implicated in causing corrosion, hydrogen sulfide and ferrous sulfide production in oilfield oil and water handling facilities.

Our invention includes novel probes for the sulfate-reducing bacteria described herein prepared on the basis of and corresponding to unique, recognizable base sequences in a portion of the 16S rRNA of an SRB of interest. Each probe has complementary base sequences that will hybridize to 16S rRNA base sequences from the bacteria of interest. The probe preferably has at least one identifiable, detectable label attached to it. Oligonucleotides that are of opposite polarity to either the target rRNA or the probe are also described. Their function is to serve as negative control probes in parallel assays with the target-specific probe, to discriminate true positives from background signal. Use of negative control probes and techniques to prevent gram positive bacteria from interfering with analyses are particularly useful with crude environmental samples.

Our invention also includes a method of assaying for the presence of sulfate-reducing bacteria in a test sample, and includes making a lysate of the bacteria contained in a test sample and binding the RNA in the lysate to a solid support. The attached test sample extract is exposed to an oligonucleotide DNA probe composed of a nucleotide sequence substantially complementary to the specific nucleotide sequence of a portion of the 16S rRNA molecule of the sulfate-reducing bacteria to be assayed. The nucleotide sequence of the probe is capable of hybridizing or base pairing with the complementary sequences of the 16S rRNA molecule to be assayed. The probe also includes a detectable label. The solid carrier plus attachments is rinsed to remove any probe not hybridized to the test sample, removing any unattached labelled probe that would otherwise interfere with correct readings. The carrier is then assayed for the presence of the probe which indicates qualitatively and quantitatively the presence of the SRB of interest. Procedures for determining total bacterial counts based on probes for portions of the 16S rRNA molecule common to all bacteria are also described.

The current method of detection of 16S rRNA nucleotide sequences relies on the probe binding to ribonucleotide sequences in the 16S rRNA molecule. Our invention utilizes specific DNA oligonucleotide probes complementary to the 16S rRNA molecule to specifically identify the sporing sulfate-reducing bacteria and a member of the non-sporing sulfate-reducing bacterium, *D. desulfuricans,* for rapid and accurate identification, both qualitative and quantitative, in a sample suspected of containing SRBs using filter, solution, or other hybridization methods employing a radioactive or non-radioactive detection system. Our filter-based detection system is based upon one used to detect messenger RNA in an RNA colony hybridization method developed by Ivanov and Gigova, *Gene* 46:287–290 (1986), adapted by us to be used with rRNA. For solution hybridizations, we used a format adapted from published European patent application 0,229,442 (Kohne and Kacien, 1987).

Our invention provides probes based on the 16S rRNA sequences capable of specifically identifying the sporing and one of the non-sporing sulfate-reducing bacteria for rapid and accurate identification, both qualitative and quantitative, in a sample suspected of containing SRBs using a filter or solution hybridization method employing radioactive or non-radioactive detection systems.

The probes included in this invention were selected or prepared, as the case may be, after sequence analysis of the 16S rRNA molecule. In some instances it was necessary to first isolate a candidate bacterium and sequence its 16S rRNA molecule as described in Lane et al., *Proc. Natl. Acad. Sci. USA* 82:6955–6959 (1985). Use was also made of sequence data available from the literature.

Once synthesized, the candidate probes were tested against partially purified RNA obtained from known SRBs using a dot blot assay with $^{32}$P-labelled DNA probes. The primary reagent is the labelled oligonucleotide DNA probe approximately of 15–31 nucleotides. The probe is substantially complementary to the 16S rRNA molecule. The probe is obtained from 16S rRNA according to published procedures and is synthesized to be complementary to a predetermined sequence to accurately target and hybridize to rRNA from the particular SRBs and groups of SRBs that are to be detected and/or quantitated. The probe is labelled with a convenient marker that is itself non-reactive, readily available, easy to use, and reliable. Ligands such as biotin, thyroxine and cortisol or other linkers may be used to attach the marker to the probe. Enzymes of interest as labels are primarily hydrolases, particularly the esterases and glycosidases, or oxidoreductases, particularly peroxidases. Fluorescent compounds useful as labels include fluorescein and its derivatives, and rhodamine and its derivatives, among others. Chemiluminescent compounds and antibodies could also be utilized in a labelling/detection system. Alternatively, the probe is labelled with a radioactive isotope such as $^{32}P$, $^{3}H$, $^{14}C$, $^{125}I$, $^{35}S$ or other such nuclide. Any radioactive label may be employed which provides for an adequate signal and has sufficient half-life.

Briefly, the procedures for identifying sulfate-reducing bacteria, or other bacteria of interest, using oligonucleotide DNA probes complementary to the 16S rRNA molecule are as follows: a sample thought to contain the SRB of interest is treated with the lytic agent to expose the 16S rRNA molecule. In one embodiment, total cellular RNA is fixed to a suitable support, e.g., a nitrocellulose or nylon membrane. Oligonucleotide DNA probes with base sequences complementary to a portion of the 16S rRNA molecule are hybridized to the rRNA, which is attached to the support. Unhybridized probe is then washed away since it is not bound to the solid support-rRNA complex. Alternatively, any method that would destroy or interfere with signal from unhybridized probe could also be used to enable detection of signal specifically from bound probe. The use of nucleic acid probes to detect SRBs is not limited to the use of any particular labelling or labelling/assay system. The label is "read" and quantified using usual procedures.

The particular hybridization technique used is not essential to the invention. Generally, substantial excess over stoichiometric amount of the probe will be employed to enhance the rate of binding to the fixed RNA in hybridization assays.

DETAILED DESCRIPTION OF AN EMBODIMENT OF THE INVENTION

Preparation of cells impinged on nitrocellulose filter paper: Cells from pure culture isolates of SRBs (positive controls) as well as from non-related bacteria, for example, *E. coli* and *B. subtilis* (negative controls), or from environmental samples, are filtered onto a nitrocellulose membrane (0.22 or 0.45 μm pore diameter). The cells may be fixed in 0.5% formalin before application. The membrane is placed on Whatman 3MM filter paper soaked in 10% sodium dodecyl sulfate (SDS) for 5 minutes at room temperature, after which it is transferred to a filter paper (Whatman 3MM) soaked in 3X SSC (1X, 0.015M sodium citrate, 0.15M sodium chloride, pH 7.6) at 65° C. for 15 minutes. A hooded slide warmer maintained at 65° C. is used for stable temperature maintainance. The nitrocellulose filter paper with the impinged cells on it is dried at 37° C. for 10 minutes, vacuum dried 15 minutes at 70° C., and stored under vacuum until use. Cells may be impinged on nitrocellulose filter paper contained in a dot blot apparatus, or on circular filters of 2.4 cm for larger volume application.

Hybridization of labelled probe target: The target (16S rRNA) from the sample to be assayed is bound to the nitrocellulose filter paper during the above treatment. The filters are prehybridized in a solution composed of 1M NaCl, 0.1% SDS and 50 μg/ml of polyA RNA for 1 hour at 65° C. Hybridization with probe end-labelled with [gamma -$^{32}P$] ATP is carried out for two hours at a temperature dependent on the nucleotide base composition of the probe as determined from the formula reviewed in Meinkoth and Wahl, *Anal. Biochem.* 138:267-284 (1984):

$$T_h = 4(G+C) + 2(A+T) - 5° C.$$

where G, C, A and T are the number of corresponding nucleotides in the probe.

The filters are then washed twice for 15 minutes each at a temperature of $T_h + 5°$ C., then air dried briefly, placed onto a cellulose acetate backing or other suitable backing, covered with Saran wrap and exposed to X-ray film at −80° C. using an intensifying screen.

The probes specific to the SRBs described herein and used with our modification of the RNA colony hybridization protocol of Ivanov and Gigova (supra) permit a lower limit of detection of about $1 \times 10^6$ cells impinged on the filter when the probe is labelled with $^{32}P$.

The probes used are specific to the 16S rRNA region of interest in the SRB or target bacteria and may be prepared as described below.

A region of the 16S rRNA molecule that is specific for the bacterial isolates that we are treating as *D. desulfuricans* was determined as follows: *Desulfovibrio desulfuricans* sequences for a region of 16S rRNA which is highy variable as described in Woese et al., *Microbiol. Rev.* 47:621-669 (1983) and Stahl et al., *Appl. and Environ. Microbiol.*, 54:1079-1084 (1988) (about bases 180-220 based on *E. coli* secondary structure) were obtained from the literature (Oyaizu and Woese, supra) for American Type Culture Collection (ATCC) 27774, and from our own sequencing for ATCC 13541 and an oilfield isolate identified as 22681B. The sequences were obtained using the method of Lane et al. (supra), in which total cellular RNA is isolated and the 16S rRNA molecule is the template for a DNA sequence complementary to the rRNA. The DNA is then sequenced using the dideoxy chain termination method, which was adapted from Sanger et al., *Proc. Natl. Acad. Sci. USA* 74:5463 (1977). Both oilfield isolate 22681B and ATCC 13541 that we sequenced show two and possibly three base differences compared to ATCC 27774 in this region of the rRNA, which makes their sequences slightly different from that previously reported for ATCC 27774. The specific sequences are shown below. (Note: numbering is based on 16S rRNA of *E. coli*, as is standard in the field, and consequently the numbers of nucleotides between two numbered positions may vary depending upon the topology of the particular rRNA).

The colons between the sequences indicate sequence identity; N represents any one of the four bases, and is probably G in 22681 B and U in ATCC 13541. The (−)

in 22681 B and ATCC 13541 at the position of ca. 214 means that the base is missing compared to the G at the same position in ATCC 27774.

Although there are a few base changes among these three isolates in this 49-base-long region, other non-spore-forming SRBs (from the data base of R. Devereux, Environmental Protection Agency, unpublished) show four or more changes. A probe complementary to bases between the arrows in the above figure, however, shows 100% sequence identity among the three isolates.

In practice, we have shown in filter hybridizations that the following probe, which was complementary to bases 198–214 of ATCC 27774 (E. coli 16S rRNA numbering system), correctly detected ATCC 13541, 22681B and other oilfield isolates that we are treating as Desulfovibrio desulfuricans. The probe sequence is as follows:

(5' ATGCAAGCAGAGGCCATC 3')

The above probe did not cross react with bacteria from other genera.

DNA probes complementary to predetermined regions of the 16S rRNA molecule may also be used to quantitate sulfate-reducing bacteria. These particular probes will be useful in determining total spore-forming SRB counts in a sample in a relatively short period of time.

Figure 1A:
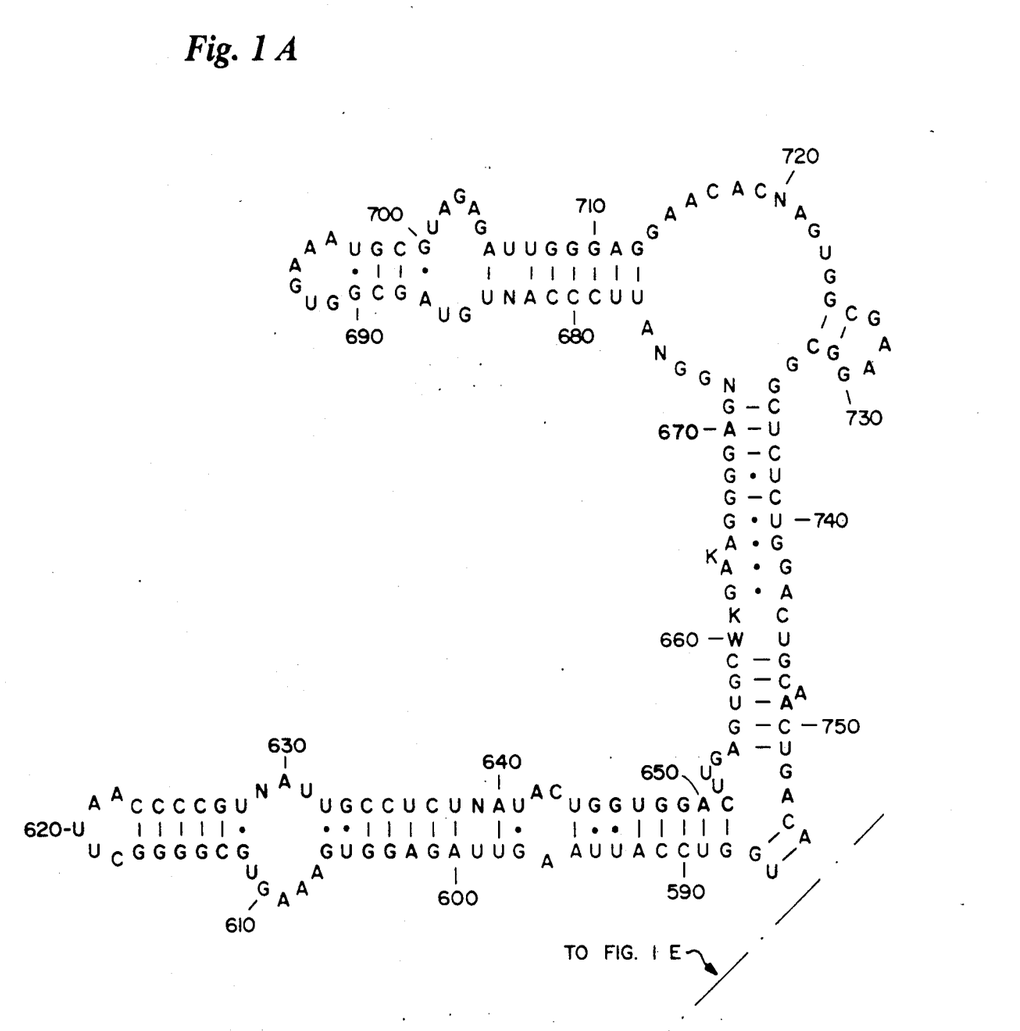
Figure 1B:
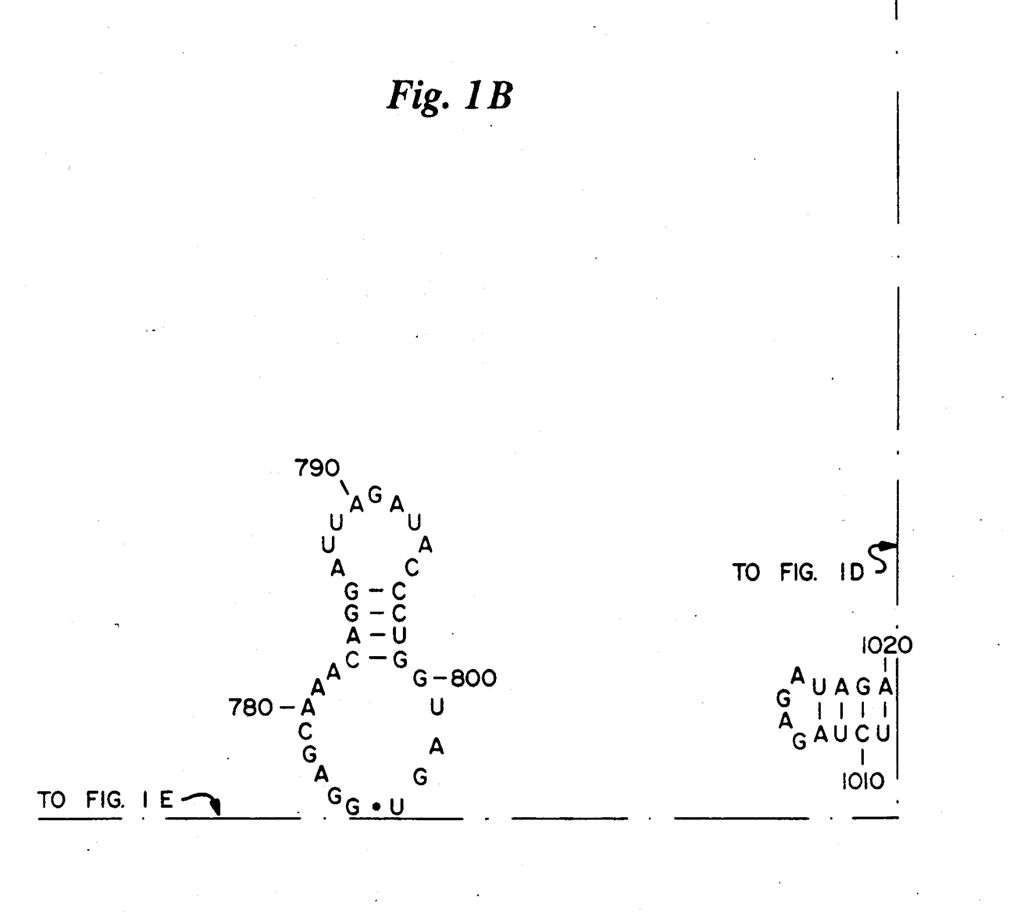
Figure 1C:
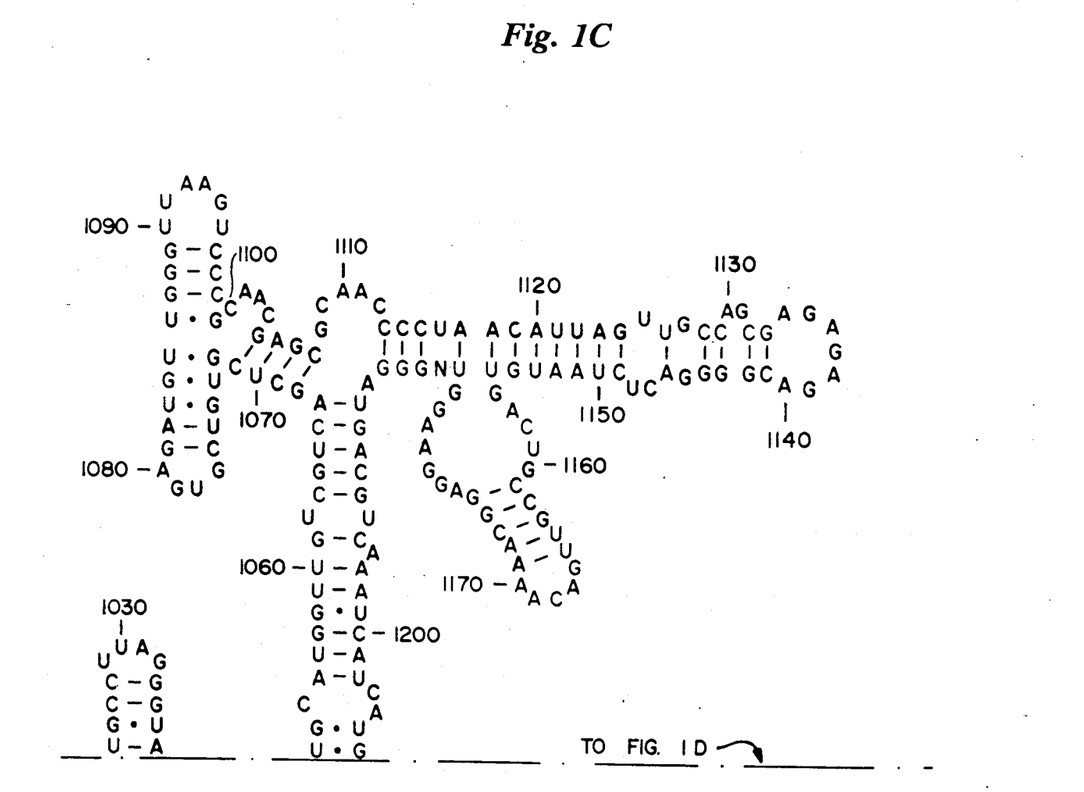
Figure 1D:
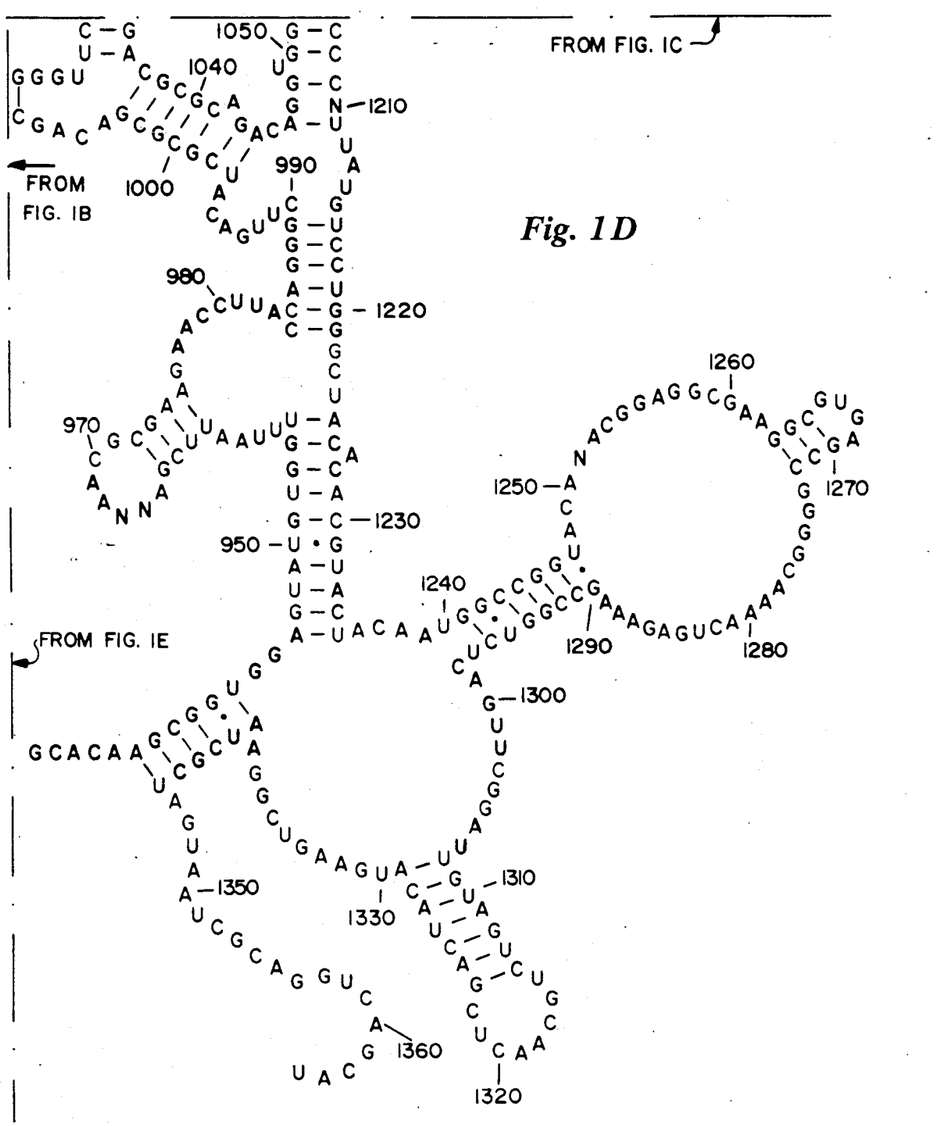
Figure 1E:
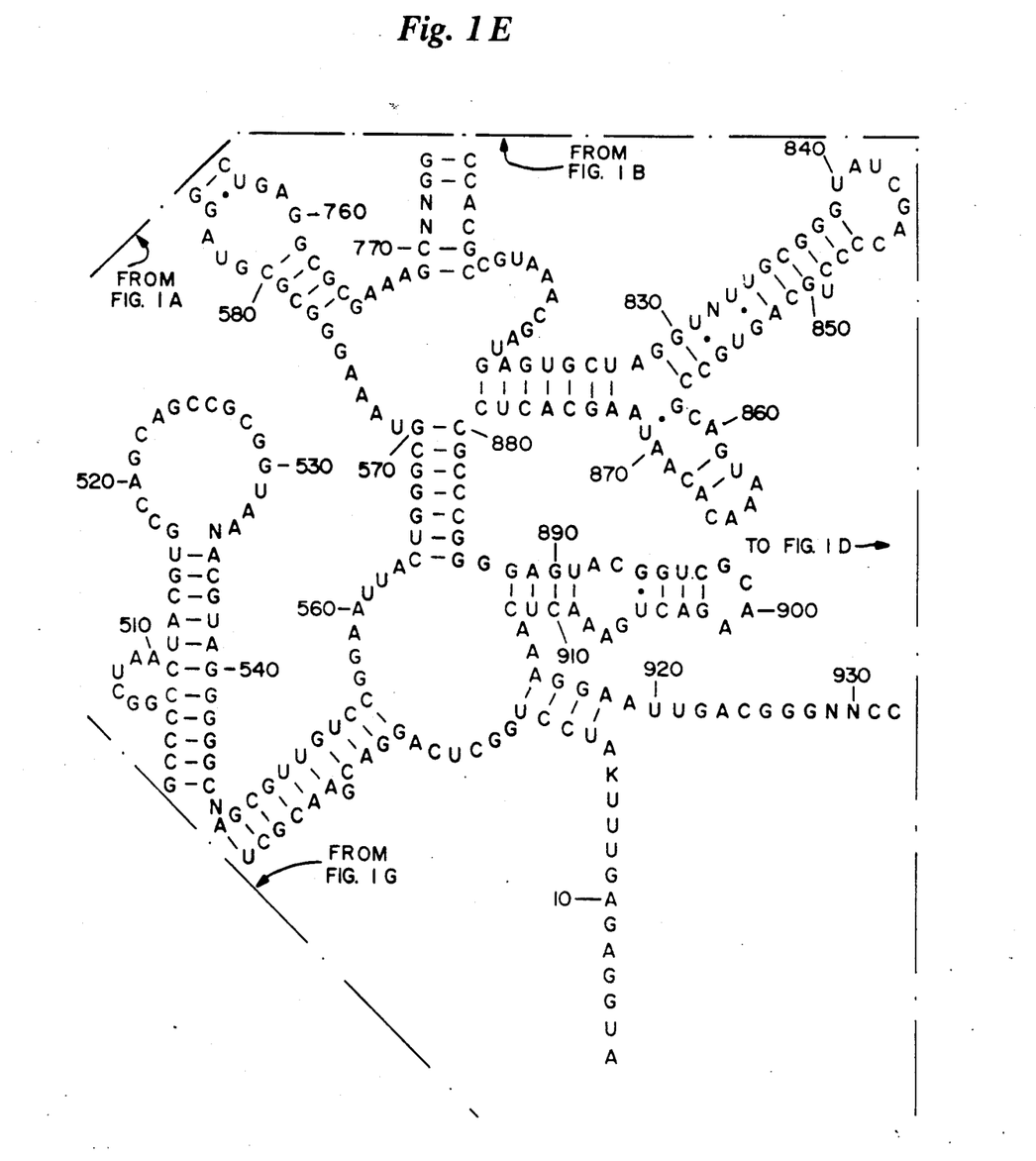
Figure 1F:
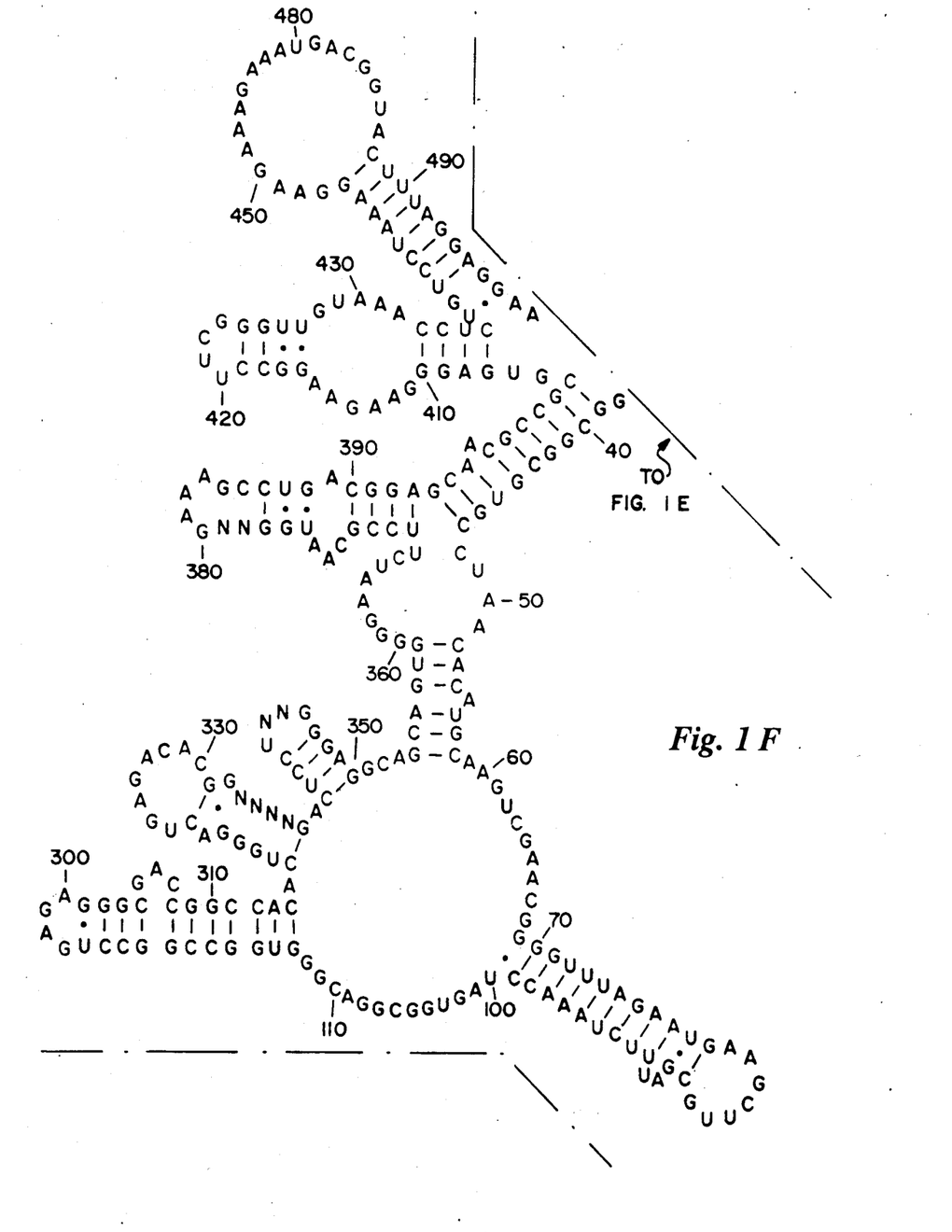
Figure 1G:
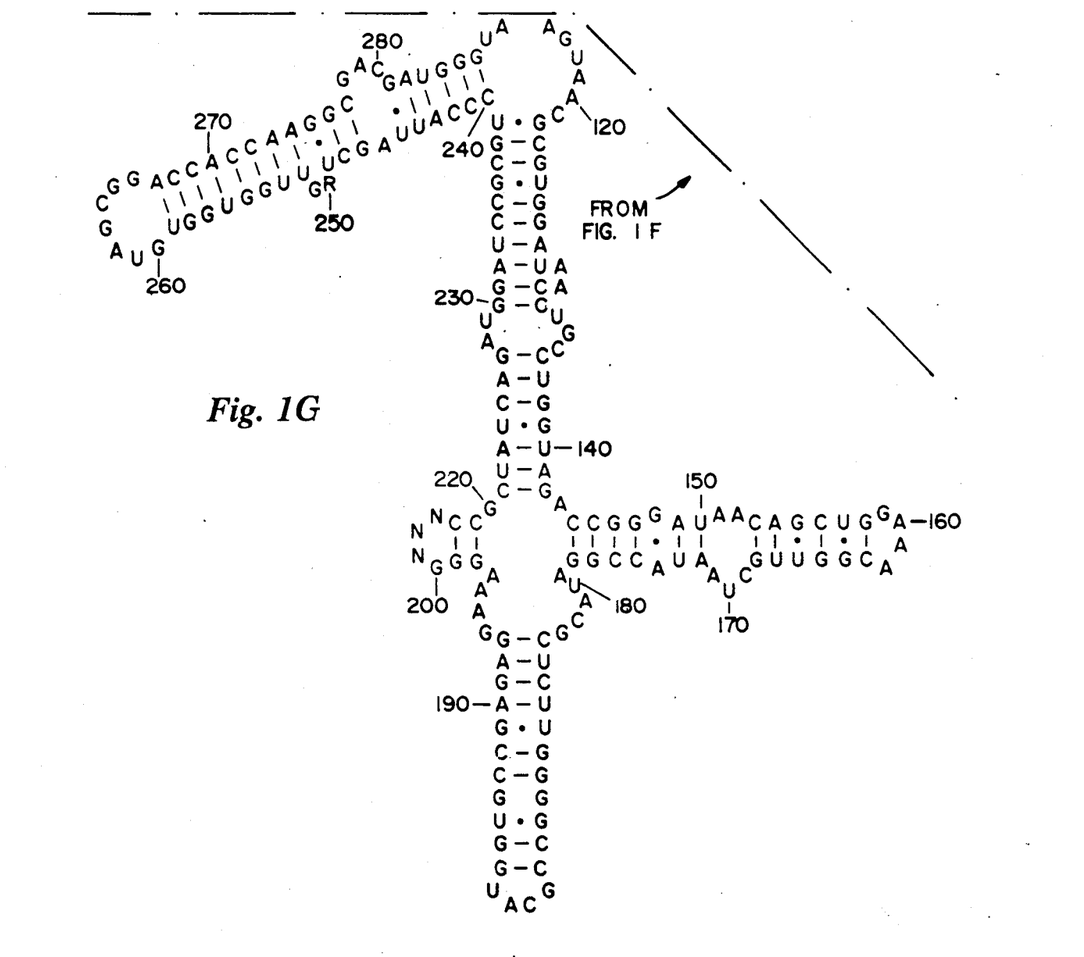

We sequenced the 16S rRNA molecule from spore-forming SRBs that were isolated from oilfield water samples and also from ATCC strains. A nearly complete 16S rRNA sequence from ATCC 19858 is shown folded into secondary structure in FIG. 1. These sequences were compared to 16S rRNA sequences available from the literature and elsewhere to locate specific nucleotide sequences that are shared in common among sporing SRBs, and not found in the 16S rRNA of other bacteria.

We identified a region of 16S rRNA sequence that can be used for detecting, quantitating, and/or distinguishing spore-forming SRBs. The sequence was shared in common among six spore-forming SRB isolates including two ATCC D. nigrificans. D, ruminis (D. ruminis sequence obtained from R. Devereux, unpublished), and three thermophilic spore-forming SRBs isolated from oilfield waters. This sequence comprises nucleotide positions 273–303 (E. coli numbering system). The sequence from which a probe was designed is:

```
273                                   303
 |                                     |
5' AAGGCGACGAUGGGUAGCCGGCCUGAGAGGG 3'
``` and the probe itself is:

```
303                                   273
 |                                     |
5' CCCTCTCAGGCCGGCTACCCATCGTCGCCTT 3'.
```

This probe, referred to here as the "spore-forming SRB probe" showed specificity against laboratory cultures of Desulfotomaculum that were retained on a filter and lysed in situ using guanidinium isothiocyanate in the protocol of Gobel et al., J. General Micro. 133:1969–1974 (1987). Lysis of the cells in guanidinium isothiocyanate followed by application of the cells to the filter gave the same result: the limit of detection was equivalent to $5 \times 10^5$ cells impinged on the filter.

The spore-forming SRB probe has been tested against isolated RNA from selected spore-forming SRB isolates as well as from two ATCC isolates. In addition, the probe was tested against isolated RNA from negative controls which included: E. coli; an isolate of Desulfovibrio desulfuricans from ATCC; and other oilfield isolates identified as Desulfovibrio. This probe successfully identified the spore-forming SRBs with minimal cross-reactivity to negative controls. Further, the sequence of the 16S rRNA molecule complementary to the spore-forming SRB probe was compared to available sequences for the same region from thirty-three 16S rRNA sequences of bacteria representing diverse eubacterial and archebacterial phyla and was found to be conserved among the spore-forming SRBs. One exception is another thermophilic spore-forming SRB, Desulfotomaculum orientis, which shows a two-base difference in this region (according to R. Devereux, unpublished). We noted that other gram-negative bacteria showed greater than 3 base changes in this region of the molecule, but that some gram-positive bacteria showed only three or fewer base differences in this region. Thus, with more extensive sequence comparisons, other gram-positive bacteria could also possibly have 100% sequence identity to the spore-forming SRBs in this region. This would not negate the general utility of this probe unless these other bacteria were present in high concentrations in the systems to be tested for SRBs. We have, however, devised a means of excluding these other bacteria from an assay should they be present in a sample also suspected of containing SRBs.

The means by which gram-positive bacteria are excluded from the gene probe assay resides in the cell lysis step preparatory to gene probe analysis. Neither guanidinium isothiocyanate nor a lysis buffer containing 20% SDS (sodium dodecyl sulfate) lysed representative gram-positive bacteria, however, both lytic agents solubilized gram-negative sporing and non-sporing SRBs. Thus, in a sample containing mixed populations of gram-positive and gram-negative bacteria, use of lytic agents that lyse only gram-negative bacteria will eliminate a possible source of false-positive signal generation coming from gram-positive bacteria.

As an illustration of this, representative gram-positive bacteria and SRBs were exposed to the lytic agents guanidinium isothiocyanate or 20% SDS. The gram positive bacteria tested were: Peptococcus isolate M06182, Proprionibacterium isolate M19782, Micrococcus isolate 21482, Bacillus subtillis (ATCC 6051, Bacillus stereothermophilus (1503 NCA), Bacillus isolate 16982, Clostridium isolate T06582, and Clostridium thermophilius ATCC 7957. The thermophiles B. stereothermophilus and C. thermophilius lysed in both lytic agents whereas the other gram positive isolates, including the thermophilic Clostridium T06582, did not.

If cells from field samples are lysed in the appropriate reagent, in this case in either guanidinium isothiocyanate or 20% SDS as summarized above, most gram positive bacteria probably will be recalcitrant to lysis. Thus, their 16S rRNA will not be available to hybridize with the spore-forming SRB-specific probe, and false-positive signal generation resulting from possible cross-reactivity of the probe is eliminated automatically.

We also constructed a probe that differentiates two sulfate-reducing spore-forming SRB thermophile isolates. A region of 16S rRNA that shows probable 100% sequence identity between two oilfield thermophilic SRB isolates previously identified as members of the genus Desulfotomaculum based on morphological and biochemical characteristics is located at bases 139–183 (E. coli numbering system). ATCC cultures of Desulfotomaculum species including *D. nigrificans, D. orientis* and *D. ruminis* show at least 5 base differences in this region. However, these two isolates differ from one another in other regions of the molecule including the region from position 180 to 220. Therefore, according to phylogenetic relationships based on 16S rRNA (Oyaizu, supra), these spore-forming SRB thermophiles show a close relatedness to each other but are enough different from ATCC type species of Desulfotomaculum and each other that they may represent new species or even a new genus. The 16S rRNA target sequences from the two thermophiles are:

Isolates:

In this representation N designates any of the 4 bases. In T1, at positions marked with a bar (|), the base is most probably A or U, and the second bar, N is most probably either base G or U. A probe made from this sequence has been tested with isolates 35282 and T1 and other spore-forming SRB thermophiles and ATCC *D. nigrificans* in the RNA cell immobilization blot hybridization described above. The probe sequence is:

where the underlined T/A means that during synthesis, either an A or a T should be inserted such that 50% of the molecules have a T at this position and 50% have an A. This probe correctly identified isolate T1 and 35282 and did not react with any of the other isolates. Thus, this probe will be useful in identifying spore-forming SRBs with this particular complementary sequence on the target 16S rRNA. As such, it will be useful in tracking some members of the thermophilic spore-forming population that are present at Prudhoe Bay and perhaps in other environments.

Both the spore-forming and D. desulfuricans-specific sulfate reducing bacterial probes described above will be used to assay cell numbers in the raw environmental samples. It will also be informative to know the total bacterial count in these samples. For this reason, another probe suited to the procedures of this invention is called Universal C. Lane et al. (supra) proposed this sequence as a "universal" primer for rRNA sequencing reactions, but did not point out that this sequence could also be used as a probe to detect phylogenetically diverse taxa. This probe identifies bacteria, archaebacteria and eukaryotes—in fact all living cells—and may be used to enumerate and quantitate total bacteria and all living cells, including fungal and yeast cells in a sample. The "Universal C" probe is:

5' ACGGGCGGTGTGTRC 3' where R is A or G.

The 16S rRNA molecule has constant and variable regions from which probes may be designed depending on the region(s) of interest. Variable regions are used to identify specific organisms in a gene probe assay, the more constant regions to identify members or groups of related organisms at higher taxanomic levels. Three relatively constant regions, termed Universal A, B and C (Lane et al., supra), have been identified and used as primers in sequence analysis of the 16S rRNA gene itself and all three primers are useful in sequencing the 16S rRNA molecule. Of these constant regions, the Universal C probe as above is the most sensitive regarding detecting its target on the 16S rRNA molecule. Its sequence position on the *E. coli* 16S rRNA, the standard for all comparisons, is 1392–1406.

We now describe using the Universal C probe as an alternative to doing total bacterial counts, such as routinely conducted in the nutrition and oil industries or anywhere a total bacterial count is needed. Because of its short time of assay, as short as 2–3 hours, as compared to 1–5 days for conventional procedures, this probe will be extremely useful.

Universal primers A, B and C were compared relative to their limits of detection using 10-fold serial dilutions of bacterial cultures (*E. coli*) in our modified RNA colony hybridization assays and detection limits were about $1 \times 10^5$ cells impinged with Universal C, which was shown to be superior to A and B. A limit of detection of $1 \times 10^4$ cells impinged on a filter was achieved with Universal C when *Pseudomonas deovorans* was tested. Universal C always identified its target in colony hybridizations of sporing and non-sporing bacteria, and was especially noted under conditions where other less sensitive probes did not identify their targets as well.

Probes can bind non-specifically to impurities in environmental samples, yielding a "false positive" result. The magnitude of the false positive signal is ascertained using "control" probes that will not bind to rRNA. Signal obtained used control probes is then subtracted from the signal obtained using the experimental probes to determine the amount of signal from true hybridization of experimental probes with rRNA. The complement of all the probes was tested against crude cell lysates in filter and solution hybridizations as well as against isolated RNA. These probes, which will not react with 16S rRNA, but will detect the gene in the genomic DNA, serve as "control" probes. Probes directed to the 16S rRNA molecule theoretically give a signal that is roughly 250–1500 times stronger than that of the complement because the 16S rRNA molecule is present at about 10,000 to 20,000 copies per cell whereas its copy in the chromosome (2 genomes per actively growing cell; Ingraham et al., supra) is present at about 14 copies per cell. If the signal from the 16S rRNA assay is real, it should theoretically be ca. 700–1400 (10,000/14–20,000/14) times greater than that of the signal from the control probe. Actual results showed a signal differential of roughly 500 fold. Control probes can thus help distinguish true positives from false positives.

Another type of negative control probe that was successfully employed is the use of an oligonucleotide identical in sequence to the rRNA "target" (except for the substitution of T for U), but of opposite polarity. We are calling this the "type I" negative control. Alternatively, the negative control probe can be constructed so that it would be complementary to the rRNA target, except that it has the same polarity. We are calling this the "type II" negative control. For example, negative controls for the Universal C probe were designed as follows:

| | |
|---|---|
| 3' TGCCCGCCACACAYG 5' | genomic DNA "anti-sense" strand |
| 5' ACGGGCGGTGTGTRC 3' | genomic DNA "sense" strand |
| 3' UGCCCGCCACACAYG 5' | target on 16S rRNA molecule |
| 5' ACGGGCGGTGTGTRC 3' | probe directed to 16S rRNA molecule (will also bind DNA "anti-sense" strand) |
| 5' GYACACACCGCCCGT 3' | negative control probe (complement of the probe, does not bind to rRNA, will bind to DNA "sense" strand) |
| 5' TGCCCGCCACACAYG 3' | Type I negative control prove (does not bind rRNA or genomic DNA) |
| 3' ACGGGCGGTGTGTRC 5' | Type II negative control probe (does not bind rRNA or genomic DNA) | where R=A or G and Y=T or C

Negative control probes will bind to neither the 16S rRNA molecule nor its gene in the genomic DNA. Negative control probes for all probes designed to detect 16S rRNA were tested in solution hybridizations described below. These probes did not bind to 16S rRNA in crude cell lysates.

The above-mentioned probes and their "negative controls," were used in a solution hybridization (adapted from Kohne and Kacien, supra), to detect spore-forming SRBs (Desulfotomaculum), or *Desulfovibrio desulfuricans*.

The following is an example of the way that nucleotide probes could be used to detect SRBs; however, there are many other possible protocols that could be used. Our invention is not limited to the use of any particular technique(s) for performing the assay such as particular hybridization conditions or techniques, solid supports used for immobilizing nucleic acids, or means of separating probe-rRNA complex from unbound probe.

SRBs were grown in liquid culture as described in Postgate, J. R., "The Sulphate-Reducing Bacteria", Cambridge University Press, Cambridge, 1981; medium C. Approximately $10^{10}$–$10^{13}$ bacteria were pelleted by centrifugation and resuspended in a minimum volume of produced water from the Prudhoe Bay oil-water handling facilities. This water had a slight oil film on the surface and contained iron oxide precipitates. The number of bacteria/ml was determined, and the sample was split into experimental and control replicates containing equal numbers of bacteria. These replicates were spun at about 7,000 g (RCF) for about 20 minutes to pellet the bacteria. This produced water "wash" was intended to simulate conditions of testing using samples drawn directly from oil-water handling facilities. Typically, each bacterial pellet was vortexed into 2–3 ml of lysing solution (20% SDS, 0.01M EDTA, 0.07M $NaH_2PO_4$, and 0.07M $Na_2HPO_4$, pH 7). The lysate was incubated at 60° C. for 10 minutes. Lysed bacterial suspensions were stable for at least a week at 4° C. with minimal decrease in assay sensitivity. The lysate was centrifuged at about 3,000 g (RCF) for about 5 minutes, and two 1 ml aliquots of supernatant were removed for hybridization. Labelled probe ($^{32}P$ end labelled) complementary to 16S rRNA was added to one aliquot and the labelled complement of the probe was added to the other aliquot. The latter probe will not hybridize to 16S rRNA and this serves as a negative control. Hybridization typically is carried out with shaking for 2 hours at room temperature. Aliquots with volumes calculated to correspond to particular numbers of bacterial cells are withdrawn for separation of unbound probe. Typically, lysate corresponding to about $10^4$–$10^{10}$ bacteria is used for each hybridization. Bound probe is separated from the hybridization solution using hydroxyapatite. Hydroxyapatite solutions are prepared by washing hydroxyapatite particles (Bio-Rad Laboratories, Richmond, CA; DNA-grade, Bio-Gel HTP), in a "phosphate wash buffer" consisting of 0.07N $NaH_2PO_4$, 0.07M $Na_2HPO_4$, 0.02% SDS, and 0.001% thimerosal, pH 7; decanting the "fines," and adding sufficient wash buffer to equal 0.02 grams hydroxylapatite per milliliter of buffer. One milliliter of this suspension is placed in a 1 ml microcentrifuge tube and spun for 1 minute at about 10,000 rpm in a microcentrifuge to pellet the hydroxylapatite (HAP). The supernatant is discarded and the hybridization mix is transferred to the tube containing the pelleted HAP. This is vortexed in a microcentrifuge shaker at room temperature for 10 minutes, spun at about 10,000 rpm in a microcentrifuge to pellet the HAP, and the supernatant is discarded. One ml of phosphate wash buffer is added to the tube, which is then vortexed for 2 minutes, spun for 1 minute, and the supernatant is discarded. This is repeated once more and the pellet is dispersed in scintillation fluid and counts per minute (cpm) are measured using a scintillation counter. Results are assessed by comparing cpm of the experimental treatment, cpm of the negative control treatment, and the cpm of a "background" treatment which contains only non-radioactive HAP spun out of the HAP-phosphate buffer suspension. If the cpm of the experimental treatment minus background is at least several times the cpm of the negative control minus background, this is regarded as a "positive result," i.e., the probe has hybridized with complementary "target" rRNA, and bacteria have been detected. When signal from experimental and control treatments approaches background, the limit of sensitivity is being approached. A minimum of about $10^5$ bacteria has been "detected" using this approach.

It would be advantageous in many circumstances to be able to detect $10^3$ or fewer bacteria per ml. This can be accomplished by centrifugation, or by filtering of large, known quantities of produced water through filters that will retain the bacteria. In this way, sufficient bacteria can be collected that sensitivity limits of the particular assay may not be a problem in the practical application of this technique.

Although this technique actually measures the number of 16S rRNA molecules from specific groups of bacteria, the signal obtained can be translated roughly into numbers of bacterial cells by comparison with results obtained using known quantities of cultured SRBs.

Solution hybridization results indicate that there is no need to proceed rapidly with the assay procedure after collection of an environmental water sample. *Desulfovibrio desulfuricans* cells were grown in culture, harvested by centrifugation, washed briefly in distilled water, and resuspended in either aerated distilled water or produced water. Assay sensitivity was not diminished by storage of the bacteria for up to 21 hours in aerated water at room temperature. This has practical utility since it would often be difficult to proceed with the assay immediately after taking a sample.

As used herein, the codes for representing the nucleotide sequences are:

| | |
|---|---|
| A = adenine | M = A or C |
| C = cytosine | R = A or G |
| G = guanine | W = A or T/U |
| T = thymine | S = C or G |
| U = uracil | Y = C or T/U |
| | K = G or T/U |
| V = A or C or G, not T/U | |
| H = A or C or T/U, not G | |
| D = A or G or T/U, not C | |
| B = C or G or T/U, not A | |
| N = A or C or G or T | |

Positions of the nucleotides are numbered in accordance with the *E. coli* numbering system.

What is claimed is:

1. A process of determining the presence of sulfate-reducing bacteria belonging to the genera Desulfovibro or Desulfotomaculum in a sample comprising the steps of:
   (a) lysing the bacteria contained in a test sample to release the bacteria's 16S rRNA molecules;
   (b) exposing the lysed sample to an oligonucleotide probe that selectively hybridizes to recognizable base sequences of a region of the 16S rRNA molecule of sulfate-reducing bacteria that is sufficienty distinctive to those bacteria that it does not hybridize to rRNA of other bacteria that may be present in the sample, the probe also including a detectable label thereon and selected from the group consisting of:

in which G/U means that either a G or a U is present at this position and -/G means that no base is present or a G is present at this position, in which T/A indicates either T or A at this position.
   (c) separating the labelled probe-rRNA complex from any labelled probe remaining in the sample that is not hybridized to the nucleic acid of the sulfate-reducing bacteria; and
   (d) determining the presence of the labelled probe hybridized to the nucleic acid of the sulfate-reducing bacteria.

2. A process for determining the total quantity of bacteria in a sample by gene probe analysis to the 16S rRNA molecule comprising the steps of:
   (a) contacting a sample to be analyzed with a 16S rRNA oligonucleotide probe having the sequence:

5'ACGGGCGGTGTGTRC 3' with an identifiable label attached to it and having complementary base sequences that hybridize to a region of the 16S rRNA molecule of the bacteria; and
   (b) detecting the quantity of labelled probe-bacteria hybrids and quantifying the total number of bacteria in the sample.

3. A process of determining the presence of sulfate-reducing bacteria belonging to the genera Desulfovibro or Desulfotomaculum in a sample comprising the steps of:
   (a) lysing the bacteria contained in a test sample to release the bacteria's 16S rRNA molecules;
   (b) exposing the lysed sample to an oligonucleotide probe that selectively hybridizes to recognizable base sequences of a region of the 16S rRNA molecule of sulfate-reducing bacteria that is sufficiently distinctive to those bacteria that it does not hybridize to rRNA of other bacteria that may be present in the sample, the probe also including a detectable label thereon, wherein the probe is selected from: an oligonucleotide probe having the nucleotide sequence from bases 273–303 of:

an oligonucleotide probe having the nucleotide sequence from nucleotides 184 to 219 of:

in which G/U means that either a G or a U is present at this position and -/G means that no base is present or a G is present at this position, an oligonucleotide probe having the following nucleotide sequence that is complementary to 16S rRNA nucleotides 198 to 214:

an oligonucleotide probe having the following probe sequence which is complementary to 16S rRNA nucleotides 141 to 164:

in which T/A indicates either T or A at this position;

(c) separating the labelled probe-rRNA complex from any labelled probe remaining in the sample that is not hybridized to the nucleic acid of the sulfate-reducing bacteria; and (d) determining the presence of the labelled probe hybridized to the nucleic acid of the sulfate-reducing bacteria.

4. The process of claim 3 in which the test sample is lysed to solubilize gram-negative sporing and non-sporing sulfate-reducing bacteria thereby excluding any gram-positive bacteria present in the sample from further analysis.

5. The process of claim 3 in which the sulfate-reducing bacteria are spore-forming.

6. The process of claim 3 in which the bacteria are non-spore-forming.

7. The process of claim 3 in which the sulfate-reducing bacteria are sporing bacteria or non-sporing bacteria of the species Desulfovibrio desulfuricans.

8. The process of claim 3 in which the probe hybridizes to a region of the 16S rRNA sequence of Desulfovibrio bacteria that is sufficiently distinctive of said sulfate-reducing bacteria that the probe does not hybridize to the 16S rRNA molecules of other bacteria that may be present in the sample.

* * * * *